United States Patent
Sairenji et al.

[11] Patent Number: 5,195,114
[45] Date of Patent: Mar. 16, 1993

[54] DIGITAL PANORAMIC RADIOGRAPHIC APPARATUS

[75] Inventors: Eiko Sairenji; Yoshinori Arai, both of Tokyo, Japan

[73] Assignee: Kabushiki Kaisha Morita Seisakusho, Kyoto, Japan

[21] Appl. No.: 769,862

[22] Filed: Oct. 1, 1991

[30] Foreign Application Priority Data

Oct. 5, 1990 [JP] Japan .................................. 2-269212

[51] Int. Cl.⁵ .............................................. A61B 6/14
[52] U.S. Cl. ........................................ 378/40; 378/39; 378/170; 378/191; 378/168; 378/205; 378/4
[58] Field of Search .................... 378/38, 39, 40, 4, 19, 378/62, 901, 170, 191, 168, 205

[56] References Cited

U.S. PATENT DOCUMENTS

| | | | |
|---|---|---|---|
| 4,823,369 | 4/1989 | Guenther et al. | 378/39 |
| 5,018,177 | 5/1991 | McDavid et al. | 378/62 |
| 5,033,070 | 7/1991 | Kanerva et al. | 378/39 |
| 5,093,852 | 3/1992 | Nishikawa et al. | 378/39 |

Primary Examiner—Constantine Hannaher
Assistant Examiner—Kim-Kwok Chu
Attorney, Agent, or Firm—Koda and Androlia

[57] ABSTRACT

The apparatus of the present invention comprising a rotary means having an X-ray source disposed opposite to an X-ray image detection section for detecting the image of the X-ray which penetrated an object to be photographed, with the object positioned therebetween, and rotating the X-ray source and the X-ray image detection section as an integrated unit around the object, an image storage means which sequentially stores image information obtained by the X-ray image detection section as frame images, and an image processing means which sequentially derives image information from the image storage means at predetermined time intervals, adds the information of each image while shifting the information of each image by a predetermined distance in the image movement direction along a series of image information to digitally form the panoramic image of a given tomographic image layer depending on the interval for deriving the information of each image and the shift amount. With this apparatus of the present invention, all information on the objects being present along the X-ray passage is included in the frame images stored in the image storage means by one photographing operation. The apparatus can form the panoramic image of a given tomographic image layer after photographing by utilizing such abundant information.

5 Claims, 3 Drawing Sheets

DIGITAL PANORAMIC RADIOGRAPHIC APPARATUS

BACKGROUND OF THE INVENTION

1. Field of the Invention

The present invention relates to an apparatus which obtains information on a given curved tomographic orbit as two-dimensional panoramic images. This apparatus can be used as a panoramic radiographic apparatus for dental treatment which photographs human dental arches. The apparatus can also be used as a tomographic apparatus which photographs human regions other than dental arches or as a tomographic apparatus for nondestructive inspection of various substances.

2. Description of the Prior Art

As this kind of apparatus, a dental panoramic radiographic apparatus which uses films is well known. The apparatus has an X-ray source disposed opposite to a film with the dental arch of a patient positioned therebetween and relatively moves the X-ray source and the film in a predetermined ratio between the rotation speed of the X-ray source and the movement speed of the film to form an X-ray image of the dental arch as a panoramic image on the film by using the X-ray which penetrated the dental arch. This kind of apparatus has various problems caused by photographic technology which uses films. To solve these problems as a primary object, the applicants of the present invention have already proposed an apparatus which obtains desired panoramic images by electrically processing X-ray penetration images without using films (for example, Japanese Patent Publication No. 2-29329).

However, the conventional radiographic method has a narrow tomographic area, making it difficult to position the patient properly. In addition, when obtaining a given tomographic image layer, it is also difficult to set the proper relative positional relationship between the film and the tomographic image layer. Furthermore, the panoramic image of only one preset tomographic image layer can be obtained by a single photographing operation and information other than the panoramic image of the preset tomographic image layer is discarded. If the image of a different tomographic image layer becomes necessary, another photographing operation is required. This increases the number of photographing operations, causing much trouble. This also increases the amount of X-ray radiation exposure dose, causing a problem when a human body, such as a dental arch, is photographed. This problem is also caused when a panoramic image is obtained by the electric processing.

Moreover, the image of an object located other than the target tomographic image layer is superimposed on the panoramic image obtained by this kind of apparatus as a blurred image. This ghost image cannot be eliminated by the conventional method.

SUMMARY OF THE INVENTION

It is an object of the present invention to solve the above-mentioned problems caused by the conventional technology. More particularly, it is an object of the present invention to provide a digital panoramic radiographic apparatus which requires only one photographing operation and thereafter can obtain the panoramic image of a given tomographic image layer. Also an object of the present invention is to provide a digital panoramic radiographic apparatus which can eliminate ghost images.

To accomplish the above-mentioned objects, the apparatus of the present invention comprises a rotary means having an X-ray source disposed opposite to an X-ray image detection section for detecting the image of the X-ray which penetrated an object to be photographed, with the object positioned therebetween, and rotating the X-ray source and the X-ray image detection section as an integrated unit around the object, an image storage means which sequentially stores image information obtained by the X-ray image detection section as frame images, and an image processing means which sequentially derives image information from the image storage means at predetermined time intervals, adds the information of each image while shifting the information of each image by a predetermined distance in the image movement direction along a series of image information to digitally form the panoramic image of a given tomographic image layer depending on the interval for deriving the information of each image and the shift amount.

With this apparatus of the present invention, all information on the object being present in the X-ray passage is included in the frame images stored in the image storage means by one photographing operation. The tomographic image layer on which a panoramic image is formed is determined depending on the interval for deriving the image information from the image storage means and the shift amount of the image information position at the time of the addition. Since the deriving interval and the shift amount can be set after photographing operation, the target tomographic image layer can be set as desired by utilizing the information included.

Therefore, the panoramic image of the desired tomographic image layer can be obtained after photographing operation. Various information obtained by a single photographing operation is not discarded but utilized effectively. This saves a lot of trouble for photographing operation and can reduce the amount of X-ray radiation exposure dose, thereby being beneficial when a human body is photographed. As a result, the present invention can provide a digital panoramic radiographic apparatus with many advantageous features.

The above-mentioned image processing means forms the image on a specific tomographic image layer as a first panoramic original image, then also forms the image on a given tomographic image layer other than the specific tomographic image layer as a second panoramic original image by using a procedure similar to the above-mentioned procedure. The second panoramic original image is then converted to a projected panoramic image generated when the second panoramic original image is projected to the above-mentioned specific tomographic image layer. The projected panoramic image is subtracted from the above-mentioned first panoramic original image to form the panoramic image of the specific tomographic image layer. The subtraction can be done by batch processing or can be done sequentially at each image formation process.

In this way, the second panoramic original image is converted to the projected panoramic image and subtracted from the first panoramic original image to form the panoramic image. This means that the adverse effect of the projected panoramic image superimposed on the first panoramic original image can be eliminated. As a result, the ghost image of the object present on the tomographic image layer other than the target tomographic image layer can also be eliminated, thereby obtaining a clear panoramic image of the specific tomographic image layer.

With the above-mentioned apparatus, the interval for deriving the image information from the image storage means and the shift amount of the image information position at the time of the addition can be selected depending on the result of the detected movement speed of the target image which moves along a series of image information. This makes the selection of the target tomographic image layer easy.

A tomographic image layer on which an image moves along a series of image information in the direction opposite to that of the image on a specific tomographic image layer is selected as the tomographic image layer other than the specific tomographic image layer, i.e., the tomographic image layer for forming the second panoramic original image.

Since the object to be photographed is mainly a dental arch in the case of a dental panoramic radiographic apparatus, the cervical vertebra, and the mandibular rami and the hard palate located opposite to the dental arch are superimposed as ghost images on the panoramic image of the dental arch. Since these objects which generate the blurred images are located opposite to the dental arch with respect to the rotation center of the X-ray source and the X-ray image detection section disposed opposite to each other, the images of the objects move in the direction opposite to that of the image of the dental arch along a series of image information. Therefore, by selecting a tomographic image layer in which an image moves along a series of image information in the direction opposite to that of the image on the specific tomographic image layer and by subtracting the projected panoramic image from the first panoramic original image, the ghost images of the cervical vertebra and other objects can be eliminated in the case of the dental panoramic radiographic apparatus, and the obtained panoramic image of the dental arch can be made clear. This can realize apparatuses with superior clinical values in the medical treatment field.

DETAILED DESCRIPTION OF THE PREFERRED EMBODIMENTS

Figure 1:
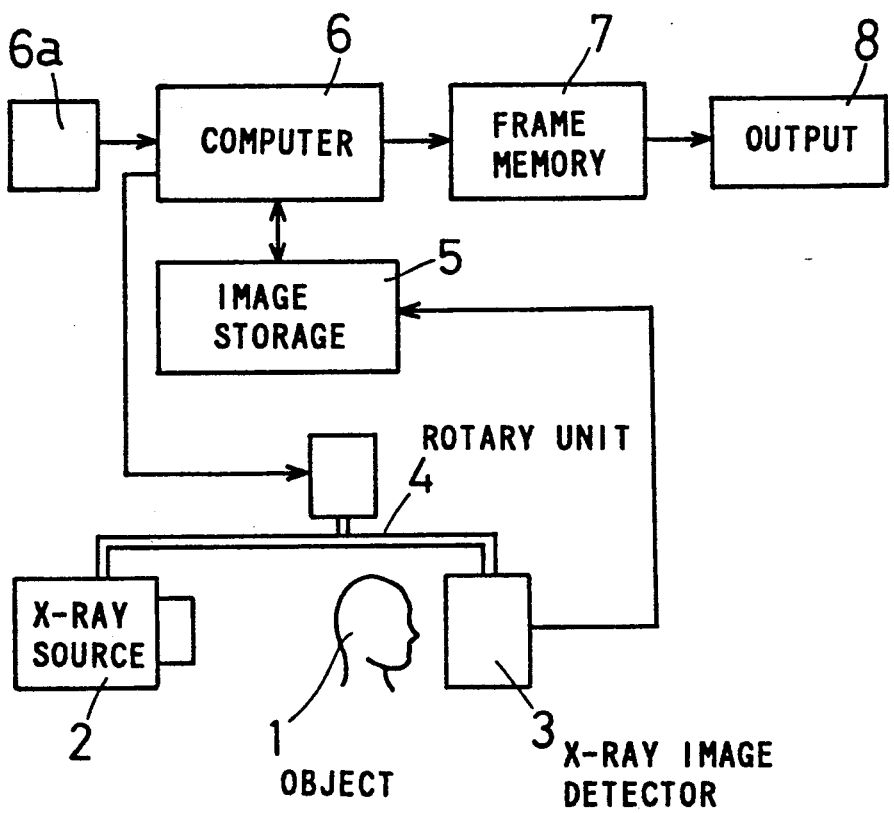
FIG. 1 is a block diagram of an embodiment of the apparatus of the present invention.

An illustrated embodiment is explained below. FIG. 1 is a block diagram of a basic embodiment of the apparatus of the present invention. Numeral 1 represents an object to be photographed, numeral 2 represents an X-ray source, numeral 3 represents an X-ray image detection section, and numeral 4 represents a rotary unit. The X-ray irradiated from the X-ray source 2 can have a cone beam shape in principle. However, to reduce the radiation exposure dose to the object 1 to be photographed, the X-ray is required to have a slit beam shape. This embodiment is structured to output X-ray with a slit beam shape, just like the X-ray of conventional apparatuses. The X-ray image detection section 3 converts the image of the X-ray which penetrated the object 1 to an electric signal which functions as a frame image having a constant area. As an X-ray image sensor, various known devices can be used: for example, a high-sensitivity camera which uses a fluorescent plate for converting X-ray to visible light and SIT (Silicon Intensified Tube) to photograph the image on the fluorescent plate, in addition to an X-ray CCD sensor, an X-ray fluorescent image intensifier, etc. The rotary unit 4 rotates the X-ray source 2 and the X-ray image detection section 3 as an integrated unit around the object 1. The rotary unit is similar to those used for conventional and known panoramic radiographic apparatuses.

Numeral 5 represents an image storage means composed of a video signal storage unit, such as a VTR or an optical disc, or a semiconductor memory device, such as large-capacity DRAM, used to continuously store the electric signals for image information obtained by the X-ray image detection section 3. Numeral 6 represents a computer. It is used as an image processing means, a key unit of the present invention, and also functions as a control unit to control the entire system. Numeral 7 represents a frame memory used to store the panoramic image obtained by the image processing at the computer 6. Numeral 8 represents an output section used to output the stored panoramic image as a visible image. An image display unit, such as a CRT display or an LCD panel, or a printer for outputting the hard copy of an image is used as the output section 8.

Figure 2:
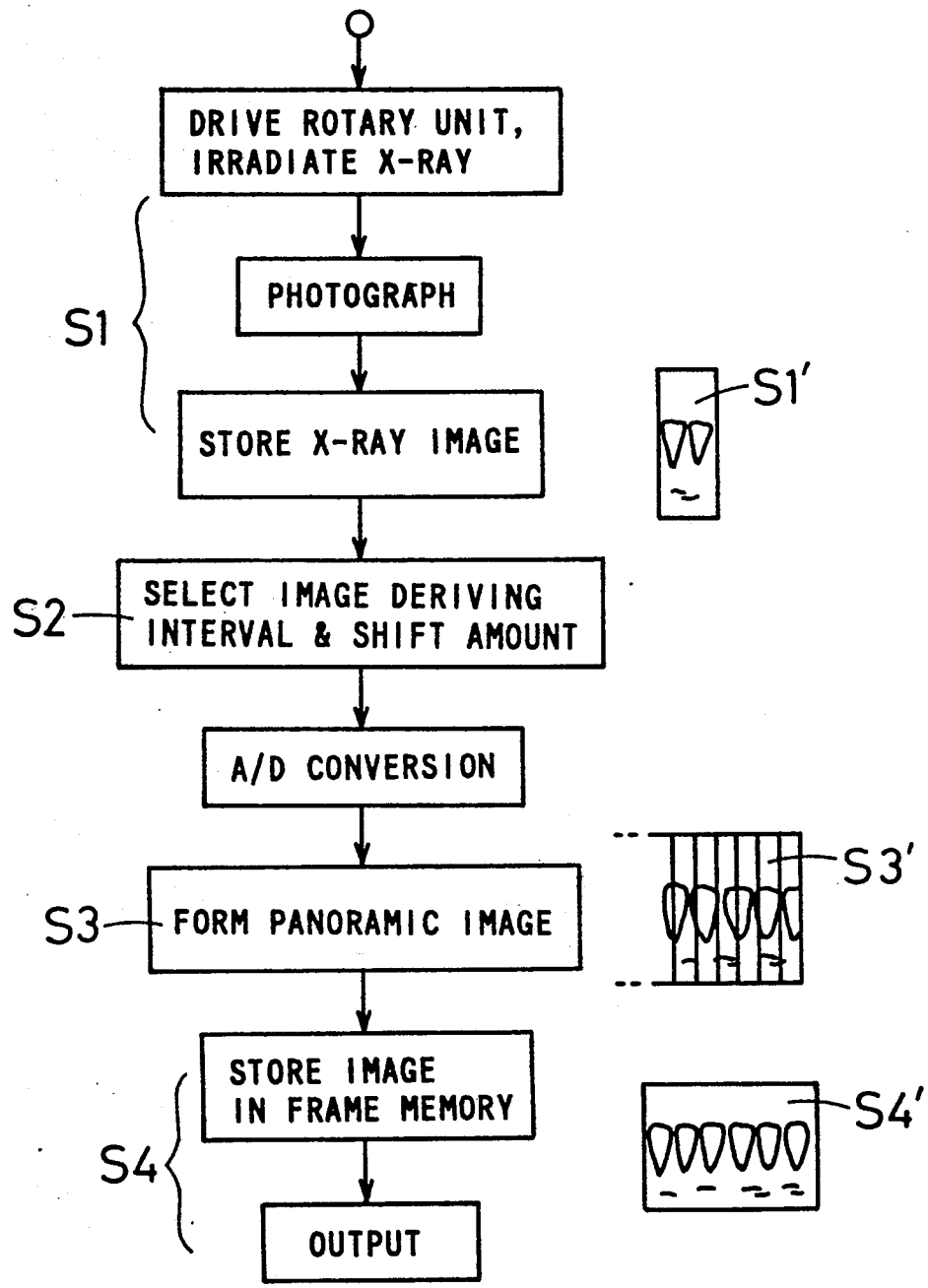
FIG. 2 is a flow chart illustrating the operation procedure of the apparatus.

FIG. 2 is a flow chart illustrating the basic operation procedure of the apparatus.

While the rotary unit 4 is being driven, X-ray is irradiated from the X-ray source 2 and the X-ray which penetrated the object 1 is received by the X-ray image detection section 3, and the obtained X-ray image information is converted to the electric signal for a frame image. As the electric signal, a type of signal similar to TV's video signal for example is used. This frame image is stored continuously by the image storage means at a rate of 30 pieces per second (step S1). The frame image is a slit image with a vertical slit corresponding to the slit beam of the X-ray. When the rotary unit 4 is rotated half around the object 1 in 30 seconds for example, a series of 900 pieces of frame images can be obtained. Instead of the above-mentioned continuous video signal, an electric signal obtained by converting short-interval intermittent photographing operation can also be used for the frame images.

The next step selects a deriving interval for selectively deriving frame images arranged at certain time intervals from a series of frame images continuously stored in the image storage means 5, and a distance (shift amount) to be added while each derived frame image is shifted by the distance in the width direction of the slit image (step S2). At the deriving intervals, the corresponding frame images are derived sequentially in the form of a digital signal and addition is performed while the position is shifted depending on the selected shift amount (step S3). The deriving interval and the shift amount in step S3 can be selected as desired. Depending on the interval and the shift amount, the panoramic image of a specific tomographic image layer can be obtained by the above-mentioned addition process. The panoramic image is then stored in the frame memory 7 and displayed or output as a hard copy by the output section 8 as required (step S4). S1', S3' and S4' are general views of the images obtained at the corresponding steps.

The fact that the panoramic image of a specific tomographic image layer can be obtained depending on the above-mentioned deriving interval and shift amount is the same in principle as the fact that the panoramic image of a specific tomographic image layer can be obtained by relatively moving the X-ray source and the film at a specified ratio in the conventional film-type panoramic radiographic apparatus. However, the apparatus of the present invention differs from the conventional apparatus in that the panoramic image of a given tomographic image layer can be formed as necessary by selecting the deriving interval and the shift amount after photographing.

Figure 3:
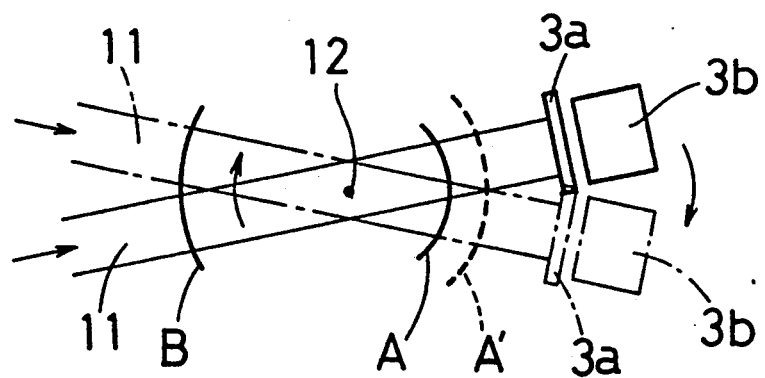
FIG. 3 is an illustration explaining how to select a tomographic image layer.

FIG. 3 explains how the panoramic image is formed by the apparatus of the present invention. When an X-ray beam 11 is rotated clockwise around a rotation center 12, the image of the object located on a tomographic image layer A is projected to the X-ray detection surface 3a of the X-ray image detection section 3 being rotated together with the X-ray beam 11 and crosses the X-ray detection surface 3a from left to right as viewed from a photographing unit 3b. In the same way, the image of the object located on a different tomographic image layer A' is projected to the X-ray detection surface 3a and crosses the surface 3a in the same direction. However, since the distance from the rotation center 12 is larger in the latter case, the movement speed at the crossing time of the image of the object located on the tomographic image layer A' is higher than that of the object located on the tomographic image layer A. Therefore, by selecting the deriving interval and the shift amount depending on the image movement speed, the panoramic image of the object located on the tomographic image layer A or A' can be formed in synchronization with the deriving interval and shift amount.

If the deriving interval and the shift amount are constant, the obtained tomographic image layer is circular as shown in FIG. 3. The deriving interval and the shift amount are not necessarily required to be constant for each processing. By changing the deriving interval and the shift amount in relation to the movement of the rotation center of the X-ray beam, a tomographic image layer comprising a plurality of image layers with different curvatures, such as the tomographic image layer C shown later in FIG. 5, can be selected.

As described above, this apparatus requires only one photographing operation and can form the panoramic image of a given tomographic image layer at any time after photographing without wasting image information including all information on the objects being present along the X-ray passage. Even if the obtained panoramic image is dislocated from the desired tomographic image layer, a proper image can be obtained by correctly performing the image processing again. Another rephotographing operation is not necessary.

The above-mentioned deriving interval and shift amount can be selected by reproducing a series of frame images continuously stored in the image storage means 5, by detecting the speed of the target image moving through the reproduced images and by judging the results of the detection. In other words, the image of the object which the X-ray penetrated is taken in the reproduced images although the image may be unclear. From the unclear image, the movement speed of the target image can be known. By measuring the speed, the values of the deriving interval and the shift amount for obtaining the panoramic image of the target tomographic image layer can be easily calculated. The selected deriving interval and shift amount are input to the computer 6 from an input unit 6a, such as a keyboard.

The tomographic image layer selected by the above-mentioned processing is not limited to the tomographic image layers A or A' on the side of the X-ray detection surface 3a, i.e., on the side opposite to the X-ray source 2, from the rotation center 12 in FIG. 3, but includes a tomographic image layer, such as the tomographic image layer B, on the side of the X-ray source 2 located on the opposite side with respect to the rotation center 12 as viewed from the X-ray detection surface 3a. In the case of the tomographic image layer B, its image crosses the X-ray detection surface 3a from right to left as viewed from the photographing unit 3b, unlike the image of the tomographic image layer A which crosses in the opposite direction. In this case, the posiion shifting direction at the time of adding each derived frame image should be reversed, that is, the shift amount should be made negative.

Figure 4:
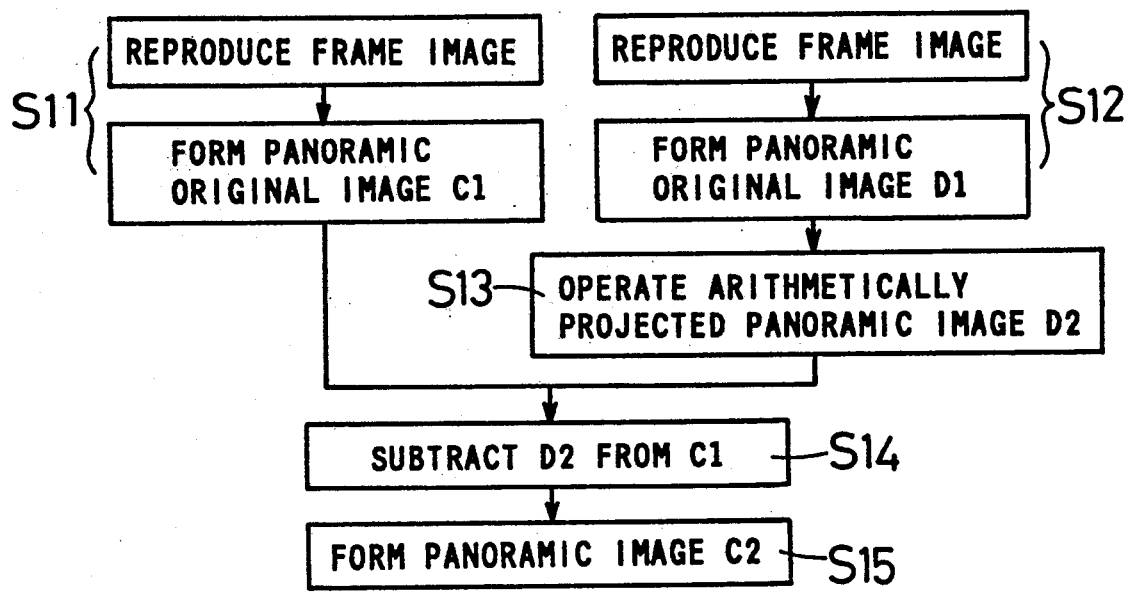
FIG. 4 is a flow chart for implementing a procedure to eliminate ghost images from a dental panoramic radiographic apparatus.

The present invention uses the above-mentioned principle to eliminate ghost images. The images of the objects on the tomographic image layer B shown in FIG. 3 are superimposed on the obtained panoramic image as horizontally moving blurred images, since the deriving interval and the shift amount of the images of the objects on the tomographic image layer B are not synchronous with those of the images on the target tomographic image layer of the panoramic image, such as the tomographic image layer A. These blurred images generate ghost images, greatly reducing the clearness of the panoramic image of the target tomographic image layer. An exemplified procedure for eliminating the ghost images from the panoramic image obtained by a dental panoramic radiographic apparatus is described below referring to FIGS. 4 and 5. In this case, the target tomographic image layer A corresponds to a dental arch 15 represented by letter C in FIG. 5 and the tomographic image layer B corresponds to a tomographic image layer D which includes a cervical vertebra 16 and two mandibular rami 17 located opposite to the dental arch 15, both of which may generate ghost images. Numeral 18 represents the locus of the rotation center of the X-ray beam 11.

First, the X-ray penetration image of the dental arch 15, the object to be photographed, is photographed by the procedure described in FIG. 2. A series of frame images is reproduced and the deriving interval and shift amount are selected; then the panoramic original image $C_1$ of the dental arch 15 on the tomographic image layer C is formed (step S11). In the case shown in FIG. 2, the obtained panoramic image is used as it is. In this step, however, the image is referred to as the panoramic original image since it is processed further. By using the same procedure, the panoramic original image $D_1$ of the cervical vertebra 16 and other objects on the tomographic image layer D is formed (step S12). The images of the cervical vertebra 16 and other objects on the tomographic image layer D move along a series of frame images in the direction opposite to that of the image of the dental arch 15.

Next, the computer simulates how the panoramic original image $D_1$ is blurred when the image is projected to the tomographic image layer C to obtain the projected panoramic image $D_2$ (step S13). This projected panoramic image $D_2$ is subtracted from the previously obtained panoramic original image $C_1$ to obtain a panoramic image $C_2$ in which the blurred images of the cervical vertebra 16 and other objects on the tomographic image layer D, that is, the ghost images of the cervical vertebra 16 and other objects are eliminated from the panoramic original image $C_1$ (step S14).

In the above-mentioned example, it is explained that the panoramic original image $C_1$ and the panoramic original image $D_1$ or the projected panoramic image $D_2$ are obtained for the entire target tomographic image layer, then the subtraction is conducted by batch processing. However, the subtraction is not limited to such a batch subtraction but other procedures can be taken. For example, subtraction is done sequentially while each image is formed concurrently, then processed partial images are composed to form the panoramic image $C_2$.

Figure 5:
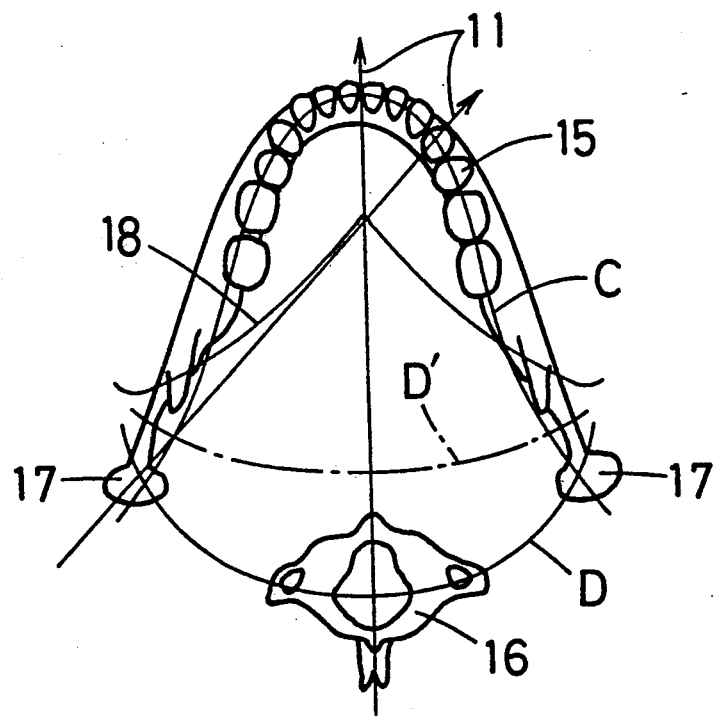
FIG. 5 is an illustration explaining the operation for eliminating the ghost images.

The ghost images can be eliminated by the processes described above. In the above-mentioned processes, the tomographic image layer D on which the cervical vertebra 16 and other objects are located actually is selected as the tomographic image layer where the panoramic original image $D_1$ is formed. However, if the tomographic image layer D' shown by a chain line in FIG. 5 is assumed to be selected, the information on the cervical vertebra 16 and other objects is also included on the tomographic image layer D'. This means that the ghost images can be eliminated even when the tomographic image layer D on which the cervical vertebra 16 and other objects are located is not selected as a tomographic image layer for forming the panoramic original image $D_1$. Therefore, it is not necessary to strictly select the deriving interval and the shift amount. This makes the elimination process easier.

Although a panoramic image for the entire mandibular section is explained in FIG. 5, if the range of the panoramic image is limited to the front tooth section, the ghost images to be eliminated are those caused mostly by the cervical vertebra 16, simplifying the elimination process.

As described above, with this apparatus the shape of the target tomographic image layer can be changed by properly selecting the image deriving interval and the shift amount in relation to the rotation center position of the X-ray beam. In other words, the desired tomographic image layer can be selected by image processing without moving the rotation center of the X-ray beam or even when the movement amount is reduced. Therefore, if the computer and the storage means have sufficient capacities, the cost of the mechanical devices of the apparatus can be reduced by simplifying its X-ray beam rotation mechanism, although the program to be used becomes complicated somewhat. On the other hand, if the rotation center of the X-ray beam is moved depending on the shape of the dental arch as in the case of the conventional film-type apparatus, the image processing by the computer can be simplified, making the program simpler and allowing the use of a computer with a relatively small capacity. As a result, either way can be selected as desired depending on the purpose or budget for the application of the apparatus.

The explanation of the embodiment of the present invention is given mainly to obtain the panoramic image of the dental arch, since the present invention was made to improve dental panoramic radiographic apparatuses. However, the present invention can also be applied to other fields, such as tomographic apparatuses for photographing other parts of the human body and those apparatuses for nondestructive inspection of other various substances as described above.

What is claimed is:

1. A digital panoramic radiographic apparatus, comprising:

a rotary means having an X-ray source disposed opposite to an X-ray image detection section for detecting the image of the X-ray which penetrated an object to be photographed, with said object positioned therebetween, and rotating said X-ray source and said X-ray image detection section as an integrated unit around said object, an image storage means which sequentially stores image information obtained by said X-ray image detection system, and an image processing means which sequentially derives electric data of image information which corresponds to each frame of the X-ray image from said image storage means at predetermined time intervals, electrically adds each electric data while shifting the position of each electric data by a predetermined distance in the image movement direction along a series of frames of X-ray image to digitally form an image on a specific tomographic image layer as a first panoramic original image, and also to form an image on a given tomographic image layer other than said specific tomographic image layer as a second panoramic original image depending on the interval for deriving said electric data of each frame of the X-ray image and the shift amount, then converts said second panoramic original image to a projected panoramic image generated when said second panoramic original image is projected to said specific tomographic image layer and subtracts said projected panoramic image from said first panoramic original image to digitally form the panoramic image of said specific tomographic image layer.

2. A digital panoramic radiographic apparatus according to claim 1, wherein said apparatus selects the interval for deriving the electric data of each frame of the X-ray image from said image storage means and the shift amount of the image information position at the time of panoramic image formation depending on a movement speed of the target image which moves along a series of frames of the X-ray image.

3. A digital panoramic radiographic apparatus according to claim 1, wherein a tomographic image layer on which an image moves along a series of frames of the X-ray image in the direction opposite to that of the image on said specific tomographic image layer is selected as said given tomographic image layer other than said specific tomographic image layer.

4. A digital panoramic radiographic apparatus according to claim 1, or 3 wherein said apparatus is used for dental treatment.

5. A digital panoramic radiographic apparatus according to claim 2, wherein said apparatus is used for dental treatment.

* * * * *